United States Patent [19]

Sparacio et al.

[11] Patent Number: 4,775,523

[45] Date of Patent: Oct. 4, 1988

[54] DENTIFRICE SACHET

[75] Inventors: Dorinda A. Sparacio, Edison; Steven W. Fisher, Middlesex; Sandra L. Schelm, Highland Park, all of N.J.

[73] Assignee: Colgate-Palmolive Company, New York, N.Y.

[21] Appl. No.: 913,784

[22] Filed: Sep. 30, 1986

[51] Int. Cl.$^4$ .......................... A61K 7/16; A61K 7/26
[52] U.S. Cl. ........................................ 424/49; 222/92; 222/107; 206/634; 206/524.1; 206/524.2; 206/524.4; 424/58
[58] Field of Search ................ 424/49, 58; 206/524.2, 206/524.4, 524.1, 634; 222/92, 107

[56] References Cited

U.S. PATENT DOCUMENTS

| | | | |
|---|---|---|---|
| 3,534,887 | 3/1968 | Ginsberg | 206/229 |
| 3,670,927 | 6/1972 | Hubbard | 206/629 |
| 4,236,625 | 12/1980 | Beguhn | 206/634 |
| 4,590,065 | 5/1986 | Piechota, Jr. | 206/524.4 |

FOREIGN PATENT DOCUMENTS 1342755  1/1974  United Kingdom .

OTHER PUBLICATIONS

Sohio, *BAREX* 210, Brochure B210-02, B210-03, Sohio Chemical Co., Cleveland, Ohio.
Khalil, *Journal of Chromatography*, 267, 101–108 (1983).

*Primary Examiner*—J. R. Brown
*Assistant Examiner*—F. T. Moezie
*Attorney, Agent, or Firm*—Robert L. Stone; Murray M. Grill

[57] ABSTRACT

A dentifrice sachet wherein the sachet which envelops the dentifrice is a plastic laminate material having a modified acrylonitrile methyl acrylate copolymer inner surface. The sachet is subject to reduced delamination when in contact with a paste or gel dentifrice.

9 Claims, No Drawings

DENTIFRICE SACHET

This invention relates to a dentifrice sachet. More particularly it relates to a laminated plastic sachet which is subject to little or no delamination when in contact with a paste or gel dentifrice.

For many years dentifrices have been commonly packaged in flexible metal containers, such as aluminum tubes, from which the dentifrice is readily extruded as a ribbon upon application of mild manual pressure.

More recently, other types of packages have been widely used for toothpastes. These include plastic dispensers operated by vacuum pressure or with a manual pump as well as flexible plastic tubes.

Because of their form retaining properties and light weight, laminated polyethylene tubes have been the tubes of commercial choice. Nevertheless, the art has encountered difficulties due to flavor loss from toothpaste when in contact with a polyethylene tube inner surface. Such difficulties have been overcome or reduced, for instance by including among the toothpaste ingredients polyvinyl pyrrolidone as an agent to reduce flavor loss, as described in U.S. Pat. No. 4,590,065 to Piechota and Sparacio of Colgate-Palmolive Company.

As an alternative or additional means to reduce dentifrice flavor loss in a plastic tube, the structure of the plastic laminate package could also be changed. In this regard, advantage could be taken of the known flavor barrier properties of the polymeric material marketed by Sohio Chemical Company as Barex®, a modified acrylonitrile methyl acrylate copolymer. Thus, with a heat-sealed laminate tube having an outside to inside structure of polyethylene terephthalate/adhesive/aluminum foil/adhesive/low density polyethylene, flavor is lost from a toothpaste toward the nearest adhesive layer; while with a heat-sealed laminate tube having the outside to inside structure polyethylene terephthalate/adhesive/aluminum foil/adhesive Barex®, flavor is substantially or essentially completely retained within the toothpaste formulation. A dentifrice tube is described in British Pat. No. 1,342,755 to Colgate-Palmolive Company of Barex® without layers laminated thereto, which provides reduced flavor loss.

An alternative form of packaging convenient for travel, is now coming into use; that is a dentifrice sachet, generally containing about 7–12 cc of dentifrice per plastic sachet package.

It is noted that G.D. Searle Company manufactured a liniment under the name Icy Hot® in a plastic sachet having a Barex® inner layer.

In dentifrice sachets, the typical ratio of interior sachet surface to toothpaste volume is from about 16:1 to about 9:1. This surface to volume ratio far exceeds the ratio of about 2.6:1 to about 0.9:1 or less which typically prevails in plastic toothpaste tubes. In situations when sachets are provided, an additional serious problem occurs with laminated polyethylene packages; that is delamination occurs.

It is an advantage of this invention that a laminated Barex®sachet readily envelops dentifrice without being subject to substantial delamination.

Other advantages of this invention will be apparent from consideration of the following disclosure.

In accordance with certain of its aspects this invention relates to a dentifrice sachet, the sachet comprising a heat-sealed laminated package having dentifrice therein, said package having a plurality of layers adhesively laminated to one another in said laminated package, the inner surface of said laminated package being an acrylonitrile methyl acrylate copolymer, modified with butadiene acrylonitrile copolymer, said sachet enveloping a dentifrice present in amount of 7–12 cc and the ratio of the interior surface of said laminated package to the volume of said dentifrice being from about 16:1 to about 9:1.

The dental base or vehicle utilized in the present invention may be in the form of a paste or gel, comprising known ingredients conventionally used in the dentifrice art.

Paste or gel dentifrices may be based on aqueous or substantially non-aqueous systems. The former will usually include substantial proportions of finely divided, solid polishing agent, surface active agent, gelling agent and some humectant vehicle, e.g., glycerine, sorbitol, polyethylene glycol of average molecular weight of about 600 and mixtures thereof and will be opaque, whereas the latter type will often be a clear gel, containing a minor proportion of a visually clear particulate solid polishing agent, a larger proportion of humectant vehicle, surface active agent and gelling agent, with a minor proportion of water (e.g. below 10% by weight) often being present.

The surface active agent, or detergent, present in the dentifrice may sometimes be cationic or amphoteric but will usually be anionic or nonionic. Of these compounds, the anionics are the most preferred. The anionic detergents or surface active agents also usually serve as foaming agents. Among the useful anionic detergents may be mentioned the higher fatty acid monoglyceride monosulfates, such as the sodium salts of the monosulfated monoglycerides of hydrogenated coconut oil fatty acid; higher alkyl sulfates, such as sodium lauryl sulfate; higher alkyl aryl sulfonates, such as sodium linear dodecyl benzene sulfonate; higher olefin sulfonates, such as sodium higher olefin sulfonate in which the olefin group is 12 to 21 carbon atoms; higher alkyl potassium sulfoacetates; higher fatty acid esters of 1,2-dihydroxypropane sulfonates, magnesium salt; the substantially saturated higher aliphatic acyl amides of lower aliphatic aminocarboxylic acid alkali metal salts, such as those having 12 to 16 carbon atoms in the fatty acyl radicals, higher alkyl poly-lower alkoxy (of 10 to 100 alkoxies) sodium sulfates; higher fatty acid sodium and potassium soaps of coconut oil and tallow, and the like. As is noted, most frequently the detergents are sulfated or sulfonated compounds. Examples of useful anionic amides which may be employed are N-lauroyl sarcosine and the sodium, potassium and ethanolamine salts of N-lauroyl-, N-myristoyl, and N-palmitoyl sarcosines. In the above descriptions, "higher" refers to chain lengths of 12 to 22 carbon atoms, preferably of 12 to 18 carbon atoms and most preferably of 12 to 16 carbon atoms. Lower means 2 to 4 carbon atoms, preferably 2 to 3 carbon atoms and most preferably, two carbon atoms.

The nonionic detergents include those containing chains of lower alkylene oxide, e.g., ethylene oxide, propylene oxide, in which there are present from 10 to 100 or more moles of lower alkylene oxide. Among such materials are the block co-polymers of ethylene oxide, propylene oxide and propylene glycol, sold as Pluronics; the alkyl phenyl polyethoxy ethanols, sold as Igepals; mixed co-polymers of ethylene oxide and propylene oxide, sold as Ucons; and various other well known nonionics derived from fatty alcohols or acids and polyethylene oxide. The amphoteric or ampholytic agents include long chain (alkyl) amido-alkylene-alkylated amine derivatives, such as "Miranols", e.g. Miranol C₂M; and cationic germicidal detergents, such as diisobutylphenoxyethoxyethyl dimethyl benzyl ammonium chloride, benzyl dimethyl stearyl ammonium chloride; and tertiary amines having a higher fatty alkyl group and two polyoxyethyene groups attached to the nitrogen thereof.

The detergents constitute about 0.5–5% and preferably 0.8 to 3% by weight of the dentifrice composition.

Toothpastes and dental gels conventionally contain substantially water insoluble polishing agents or abrasives which are compatible with the formulation, in amounts from about 15–75% by weight of the total gel or paste formulation. Suitable polishing agents include anhydrous dicalcium phosphate, dicalcium phosphate dihydrate, tricalcium phosphate, insoluble sodium methaphosphate, crystalline silica, colloidal silica, complex aluminosilicates, aluminum hydroxide (including alumina trihydrate or hydrated alumina), magnesium phosphate, magnesium carbonate, calcium carbonate, calcium pyrophosphate, bentonite, talc, calcium silicate, calcium aluminate, aluminum oxide, aluminum silicate, and silica xerogels and hydrous gels. Most of the polishing agents mentioned are most useful in the preparation of opaque dentifrices but some of them, such as colloidal silicas, especially the silica xerogel and hydrous colloidal silicas, as well as complex sodium aluminosilicates, including those characterized as containing a low (e.g. about 0.7–1.5% by weight) of combined alumina, may be utilized in the manufacture of clear gel dentifrices, because their indices of refraction approximate those of other dentifrice constituents, particularly of the liquid vehicle. If desired, clear gel dentifrices may be made less clear or opacified by including therein, opacifying agent and/or substantial water content (e.g. at least about 10% by weight). When gel dentifrice is employed in the present invention, prevention of delamination and flavor retention is excellent. When a cream dentifrice is employed, substantial improvement in reducing delamination and flavor loss is observed compared to the situation when polyethylene sachet is used.

In dental gel or toothpaste dentifrice formulations, the liquid vehicle and solids should necessarily be proportioned to form a gel or creamy mass of desired consistency, which for instance is readily extrudible from a opened sachet upon application of mild manual pressure. In general the liquids in the dental gel or toothpaste will comprise chiefly water, glycerine, sorbitol, polyethylene glycol 400 or 600 or propylene glycol, including suitable mixtures thereof, such as glycerine and sorbitol in a weight ratio of about 0.25:1 to about 3:1, typically about 0.25–1 to about 0.8–1. It is advantageous usually to use a mixture of both water, and a humectant such as glycerine, or sorbitol or mixtures thereof. The total liquid content will generally be about 20–75% by weight of the formulation. In gel dentifrices the amount of water (excluding that water which may be used to dissolve sorbitol) is often below 10% by weight, e.g., about 2–5%. In paste dentifrices, the amount of water generally is at least 10%, typically about 15–25%. It is preferred to use also a gelling agent in dental creams such as the natural and synthetic gum-like materials, e.g. Irish Moss, gum tragacanth, sodium carboxymethylcellulose, polyvinylpyrrolidone, iota-carrageenan, xanthan gum or starch. Irish Moss and sodium carboxymethylcellulose are compatible particularly and are preferred gelling agents. The gelling agent or gum content is usually in an amount up to about 10% and preferably about 0.3–5% by weight of the formulation. Fillers such as pyrogenic silica and silica aerogel may also be used, typically in amounts up to about 10% by weight to supplement the gelling agent, particularly in dentifrices. These colloidal silica aerogels which include Syloid® 244 and 266 and Aerosil®, and the pyrogenic silica sold as Cab-O-Sil® may be used as thickening agents, typically, in amount of about 5–10% by weight. The silica, Sylox® 15 is also a desirable thickener.

Any suitable flavor oil or mixture thereof may be used in this invention. Examples of flavor oils include oils of spearmint, peppermint, wintergreen, sassafras, clove, sage, eucalyptus, marjoram, cinnamon, lemon and orange. The flavoring oils are water-insoluble and are emulsified into the dentifrice formulation under moderate agitation in amounts of 0.01 to 5% by weight and preferably about 0.5–3% by weight, and most preferably about 0–5.3% by weight. Desirably, the flavor contains a mixture of spearmint and peppermint oils (typically, about 3:1 to 1.3 by weight) which may be supplemented with alpha-ionone, wintergreen or the synthetic substantial equivalent thereof, methyl salicylate, and the like.

Various other materials may also be incorporated into the dental vehicle. Examples thereof are fluorine-containing compounds such as stannous fluoride, potassium stannous fluoride ($SnF_2KP$), sodium hexafluorostannate, stannous chlorofluoride, sodium fluoride and sodium monofluorophosphate. These materials, which dissociate or release fluorine-containing ions in water, may be resent in the dental vehicle in an effective, but nontoxic amount, usually within the range of about 0.1–5% by weight. Other additives include preservatives such as sodium benzoate, chlorophyll compounds, silicones, ammoniated materials such as urea and diammonium phosphate, antibacterial agents such as benzethonium chloride and other quaternary antibacterial compounds, sweeteners such as sodium saccharin sodium cyclamate or the like and coloring and opacifying agents. These additives may be used in amounts which do not adversely affect the properties and characteristics of the dentifrice in accordance with present invention. Each constituent may be present in minimal amounts of up to a maximum of 5% by weight and preferably up to 1% by weight of the formulation.

The combination of sodium fluoride, pyrophosphate, for instance from a mixture of tetrapotassium pyrophosphate and tetrasodium pyrophosphate and a copolymer of maleic anhydride and polymethyl vinyl ether, available from GAF Company under the trademark Gantrez®, is particularly desirable for inclusion in the dentifrice in order to reduce calculus formation.

The dentifrice typically has a pH of about 4–10, preferably about 5.5 to 8.5.

The dentifrice of this invention is prepared by conventional methods of making toothpaste and dentifrice gel. More specifically, a toothpaste may be prepared by forming a gel with carboxymethylcellulose and water, adding thereto with mixing the powdered materials and humectant, followed by the addition with mixing of polishing agent, then the surfactant and then the flavor oil. The dentifrice is then placed into a laminated plastic sachet having an inner layer of Barex® plastic, which sachet is then heat-sealed to completely envelop the dentifrice.

The sachet which is employed generally has the structure of "one dose" packages which are provided in industry for purposes such as dispensing pharmaceuticals or cosmetics in a sanitary manner, to contain food condiments such as ketchup, mustard, mayonnaise, etc. in amount suitable for use during a single meal and the like.

A disposable or throw-away type packet containing a disposable toothbrush coated with a toothpaste and enclosed in an envelope was described in U.S. Pat. No. 2,512,001. In U.S. Pat. No. 3,534,887 a disposable denture care packet was described and in U.S. Pat. No. 3,670,927 a sealed envelope for supplying dosage amounts of oral hygenic liquid compositions was described.

In U.S. Pat. No. 4,236,652 plastic laminate dispenser package for small amounts of flowable products such as foods, wherein an interior surface is composed of an imperforate, uniaxially oriented polymeric film such as Barex ® is described. In the present invention the entire interior surface is composed of such a barrier layer.

In a desirable sachet of the present invention, the flexible top layer of the sachet package may be comprised of flexible plastic sheeting such as polyethylene, paper, polyesters such as polyethylene terephthalates, cellophane, polypropylene and combinations of such materials in multi-layered laminations. Similarly, the flexible material may be coated with plastic coatings to convey specific characteristics, as desired. In a preferred embodiment the upper layers comprise a multi-layer structure of polyethylene or polyethylene terephthalate polymer with a metal foil adhesively secured thereto. The foil is preferably coated on both sides with heat sealable adhesive lacquers or otherwise conditioned to improve adhesion.

The bottom or inner layer constituting the rigid or semi-rigid face of the package is a uniaxially oriented copolymer of acrylonitrile-methacrylate with butadiene-acrylonitrile copolymer, for instance available commercially as Barex ® from Sohio.

The sachet package may be transparent or opaque. Two laminates are adhered together, generally by heat sealing to envelop the dentifrice packaged therein. At least one of the laminated portions is scored for easy opening by tearing, bending or folding. If desired, a line of ink may be printed on the film in the area superimposed over the scored area and printed indicia may direct the consumer on how to best tear, fold or bend the package to open it. The laminate bearing the scoring may be fully scored throughout the laminate structure or it may be scored only in the outer portion of the laminate with the bottom layer remaining imperforate prior to opening as described in U.S. Pat. No. 4,236,652.

A typical example of resins available as Barex ® which may be employed in the sachet packages of the present invention is the nitrile-rubber modified acrylonitrile-methyl acrylate copolymer Barex ® 210, which is about 73-77 parts by weight acrylonitrile and about 27-23 parts by weight methyl acrylate modified with about 8-10 parts by weight of a butadieneacrylonitrile copolymer which is about 70% by weight derived from butadiene. In the Journal Chromatography, 267 (1983), Pages 101-108, "Interaction Between Low-Molecular-Weight Compounds and Nitrile-Based Polymers", Khalil et al, the molecular weights of Barex ® 210 and Barex ® 200 are set forth as 90,000 and 150,000, respectively (Page 103, Table I).

The top and bottom laminates of the sachet are each generally about 50-100 microns thick. Typically the flexible outer layer, for instance of polyethylene terephthalate is about 10-15 microns thick. The intermediate metal foil, preferably aluminum, is typically about 5-20 microns thick and the adhesives on each side of the foil may be about 15-25 microns thick for the adhesive to the flexible outer layer and about 2-5 microns thick to the inner barrier layer.

The following illustrative examples are further illustrative of the nature of the present invention but it is understood that the invention is not limited thereto. All amounts and proportions are by weight except as otherwise indicated.

EXAMPLE 1

The following gel dentifrice is prepared:

|  | Parts |
| --- | --- |
| Glycerine | 25.00 |
| Sorbitol (70%) | 38.29 |
| Polyethylene Glycol 600 | 3.00 |
| Sodium Carboxymethyl Cellulose | 0.35 |
| Sodium Benzoate | 0.50 |
| Sodium Monofluorophosphate | 0.76 |
| Sodium Saccharin | 0.20 |
| Water (Deionized) | 3.00 |
| Titanium Dioxide | 0.50 |
| Silica containing 1% combined alumina | 18.00 |
| Silica Aerogel (Syloid 244) | 5.00 |
| Calcined Alumina | 2.00 |
| Color Solution (0.1%) | 0.70 |
| Sodium Lauryl Sulfate | 1.20 |
| Flavor | 1.00 |
| pH 6.5 | |
| Specific Gravity | 1.36 |

Separate portions of 12.8 grams, corresponding to 9.41 cc of the above gel dentifrice are placed in sachets having an inner layer of the acrylonitrile methyl acrylate copolymer modified with butadiene-acrylonitrile copolymer sold under the name Barex ®210 and in sachets having an inner layer of low density polyethylene (Density=0.925 g/cc) and the sachets are then heat sealed. The surface of the sachets in contact with the gel dentifrice is 112 $cm^2$, providing a plastic surface to detifrice volume ratio of 13.1:1. (Sachet surface based on 2 interior sides.)

The structure of the Barex ® sachet from outer layer to inner layer is as follows:

|  | Thickness in Microns |
| --- | --- |
| Polyethylene Terephthalate | 12 |
| White Low Density Polyethylene | 18 |
| Adhesive | |
| Aluminum Foil | 9 |
| Adcoat ® Adhesive (Morton Thiokol) | 3 |
| Barex ® Copolymer | 51 |

The structure of the polyethylene sachet from outer layer to inner layer is as follows:

|  | Thickness in Microns |
| --- | --- |
| Polyethylene Terephthalate | 12 |
| Ethylene Acrylic Acid | 21.3 |
| Aluminum Foil | 15-17 |
| Adcoat ® adhesive (Morton Thiokol) | 3.3 |
| Low Density Polyethylene | 25.4 |

The Barex ® sachets containing the gel dentifrice retain their integrity very well over a period of 24 weeks at room temperature and 9 weeks at 49° C., while the dentifrice also remains phase and flavor stable. On the other hand the sachets containing the gel dentfrice having an inner layer of polyethylene quickly undergo delamination within 4 weeks at room temperature and within 3 weeks at 49° C., while the dentifrice also did not remain phase and flavor stable. Similar extensive delamination occurs even when the inner polyethylene layer is twice as thick as 25.4 microns or more.

EXAMPLE 2

Observations corresponding to those set forth in Example 1 in Barex ® sachets sachets are observed when 12.8 g, corresponding to 9.34 cc of the following high water gel detifrice is packaged in the same sized sachets (surface to dentifrice volume ratio=12:1):

|  | Parts |
|---|---|
| Glycerine | 15.000 |
| Sorbitol (70%) | 19.657 |
| Polyethylene Glycol 600 | 5.000 |
| Iota Carrageenan | 0.600 |
| Tetrapotassium Pyrophosphate | 4.500 |
| Tetrasodium Pyrophosphate | 1.500 |
| Maleic anhydride/Polymethyl Vinyl Ether Copolymer (Gantrez S-97) (15% Solution) | 6.670 |
| Sodium Fluoride | 0.243 |
| Sodium Saccharin | 0.400 |
| Titanium Dioxide | 0.200 |
| Water (Deionized) | 20.530 |
| Hydrous Silica Gel | 16.000 |
| Silica Aerogel | 7.700 |
| Sodium Lauryl Sulfate | 1.200 |
| Color Solution (0.5%) | 0.050 |
| Flavor | 1.150 |
| pH 7.00 |  |
| Specific Gravity | 1.37 |

EXAMPLE 3

15 g corresponding to 10 cc of the following paste dentifrice are packaged in the Barex ® sachet described on Example 1 which is sized the same as in Example 1:

|  | Parts |
|---|---|
| Deionized Water | 24.49 |
| Glycerine (99.5%) | 22.00 |
| Sodium Monofluorophosphate | 0.76 |
| Carboxymethylcellulose Sodium Salt | 1.00 |
| Tetrasodium Pyrophosphate | 0.25 |
| Sodium Saccharin | 0.20 |
| Sodium Benzoate | 0.50 |
| Sodium Lauryl Sulfate | 1.20 |
| Dicalcium Phosphate Dihydrate | 48.76 |

-continued

|  | Parts |
|---|---|
| Flavor | 0.89 |
| Specific Gravity | 1.5 |

Barex ® sachet layers remain essentially laminated to each other with little loosening of layers.

It is understood that the foregoing detailed description is given merely by way of illustraton and that variations may be made therein without departing from the spirit of the invention.

We claim:

1. A dentifrice sachet, the sachet comprising a heat-sealed laminated package having dentifrice therein, said package having a plurality of layers adhesively laminated to one another in said laminated package, the inner surface of said laminated package being on acrylonitrile methyl acrylate copolymer modified with butadiene-acrylonitrile copolymer, said sachet enveloping a dentifrice present in amount of 7–12 cc and the ratio of the interior surface of said laminated package to the volume of said dentifrice being from about 16:1 to about 9:1.

2. The dentifrice sachet claimed in claim 1 wherein said dentifrice is a gel dentifrice which comprises about 15–75% by weight of a colloidal silica or complex sodium aluminosilicate polishing agent.

3. The dentifrice sachet claimed in claim 1 wherein said dentifrice is a toothpaste.

4. The dentifrice sachet claimed in claim 1 wherein said dentifrice contains about 0.5–3% by weight of a flavor oil.

5. The dentifrice sachet claimed in claim 2 wherein said gel dentifrice contains about 0.8–1.3% by weight of a flavor oil.

6. The dentifrice sachet claimed in claim 5 wherein said flavor oil comprises a mixture of peppermint and spearmint oils.

7. The dentifrice sachet claimed in claim 1 wherein the layers of said laminated package from outer layer to inner layer having surface in contact with said dentifrice are: (1) polyethylene terephthalate; (2) adhesive; (3) aluminum foil; (4) adhesive; (5) acrylonitrile methyl acrylate copolymer.

8. The dentifrice sachet claimed in claim 7 wherein said layer of acrylonitrile methyl acrylate copolymer has a thickness of about 51 microns.

9. The dentifrice sachet claimed in claim 1 wherein said copolymer has a molecular weight of about 90,000 and contains about 74–77 parts by weight acrylonitrile and about 27–23 parts by weight methyl acrylate in the acrylonitrile-methyl acrylate copolymer and about 8–10 parts by weight of the butadiene-acrylonitrile copolymer, wherein about 70% by weight thereof is derived from butadiene.

* * * * *